United States Patent [19]

Mims

[11] 3,965,573
[45] June 29, 1976

[54] AUTOPSY APPARATUS FOR ASSISTING THE CUTTING OF BRAIN TISSUE

[75] Inventor: George P. Mims, Memphis, Tenn.

[73] Assignee: Sandra J. Vorus, Memphis, Tenn.

[22] Filed: Mar. 24, 1975

[21] Appl. No.: 561,186

[52] U.S. Cl. .................................. 30/124; 30/286; 83/764; 269/60; 269/309; 269/322
[51] Int. Cl.² ...................... B26B 11/00; B26B 29/02
[58] Field of Search ...................... 30/124, 286, 114; 83/764, 765; 269/322, 295, 60, 87.1, 87.2, 309, 327

[56] References Cited
UNITED STATES PATENTS

| | | | |
|---|---|---|---|
| 622,898 | 4/1899 | Lehy | 30/124 |
| 835,892 | 11/1906 | Schipke | 269/87.1 |
| 1,892,861 | 1/1933 | Welty | 30/124 X |
| 2,104,278 | 1/1938 | Schultz | 269/87.1 X |
| 2,863,479 | 12/1958 | Macala | 30/124 X |
| 3,058,503 | 10/1962 | Perakis | 83/764 |
| 3,816,919 | 6/1974 | Portnoy | 30/124 |

FOREIGN PATENTS OR APPLICATIONS

| | | | |
|---|---|---|---|
| 248,587 | 1/1912 | Germany | 269/309 |
| 36,127 | 1/1914 | Sweden | 269/322 |

Primary Examiner—Al Lawrence Smith
Assistant Examiner—J. T. Zatarga
Attorney, Agent, or Firm—John R. Walker, III

[57] ABSTRACT

An autopsy apparatus having a portion that holds and restrains brain tissue to allow an autopsy knife to be easily passed through the brain tissue and having a portion that guides the autopsy knife through the brain tissue as the brain tissue is restrained. The portion that holds the brain tissue is preferably movable relative to the portion that guides the autopsy knife to allow the autopsy knife to be guided through any selected area of the brain tissue.

6 Claims, 3 Drawing Figures

AUTOPSY APPARATUS FOR ASSISTING THE CUTTING OF BRAIN TISSUE

BACKGROUND OF THE INVENTION

1. Field of the Invention

This invention relates generally to devices for use in autopsies and more specifically to an apparatus for assisting the cutting of brain tissue during an autopsy.

2. Description of the Prior Art

Heretofore, the cutting of brain tissue during an autopsy has been done by simply placing the brain tissue on a flat, horizontal surface such as a table or cutting board and using a standard autopsy knife to pass through the brain tissue. However, due to the physical properties of the brain tissue, difficulties arise when this procedure is used. More specifically, brain tissue is a slippery, gelatinlike substance which is extremely difficult to cut accurately because of the tendency of a knife to slip on the brain tissue and the tendency of the brain tissue to give-in when pressure is applied to it.

SUMMARY OF THE INVENTION

The present invention is directed towards alleviating the problems associated with the cutting of brain tissue during an autopsy. The concept of the present invention is to provide an apparatus for use in autopsies having a holding means for holding brain tissue and restraining movement thereof while an autopsy knife is passed through the brain tissue and having guide means located adjacent the holding means for guiding the autopsy knife through the brain tissue as the brain tissue is restrained on the holding means. The holding means preferably includes a platform member for supporting the brain tissue. The platform member is preferably movable relative to the guide means for allowing the brain tissue supported on the platform member to be positioned at different locations relative to the guide means thereby allowing the autopsy knife to be guided through a specific area of the brain tissue supported on the platform means.

DESCRIPTION OF THE PREFEERRED EMBODIMENT

Figure 1:
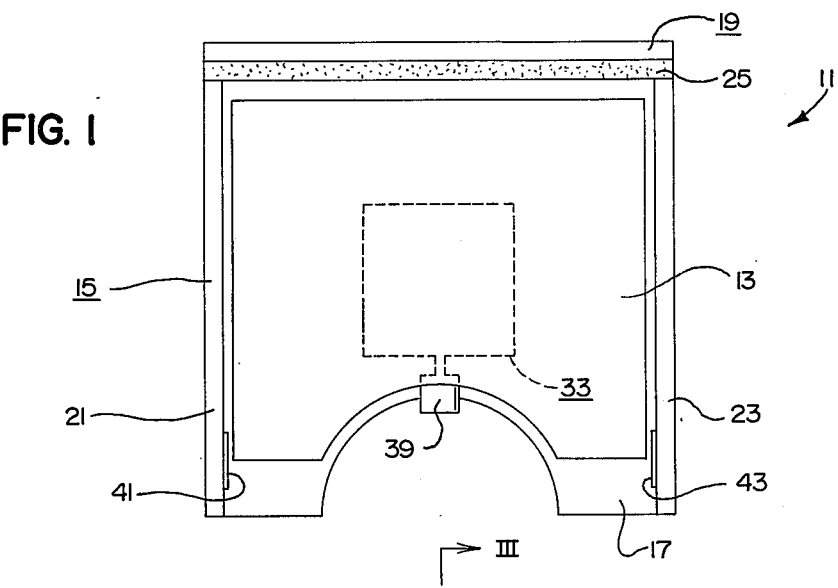
FIG. 1 is a top plan view of the autopsy apparatus of the present invention.
Figure 2:
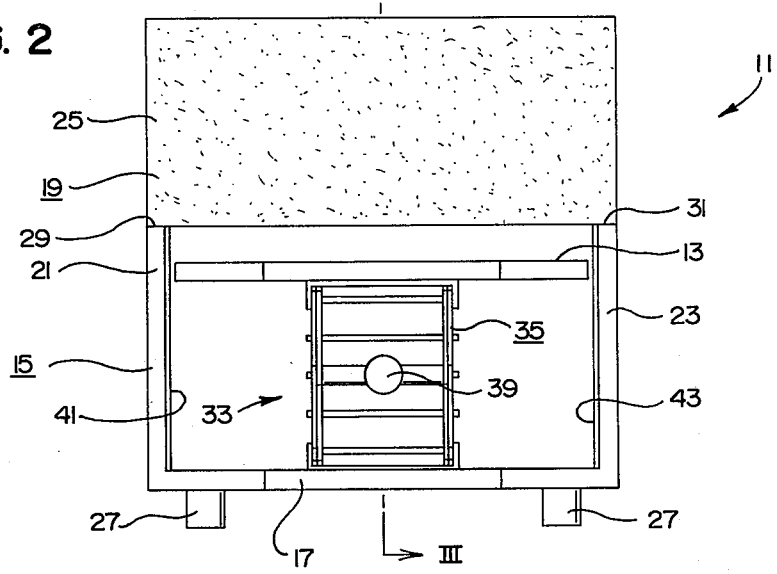
FIG. 2 is a front elevational view of the autopsy apparatus of the present invention.

The autopsy apparatus 11 of the present invention is for use in assisting the cutting of brain tissue with a standard autopsy knife during an autopsy. In general, the apparatus 11 includes holding means for holding a restraining movement of the brain tissue as the autopsy knife is passed through the brain tissue and guide means located adjacent the holding means for guiding the autopsy knife through the brain tissue as the brain tissue is restrained by the holding means.

The holding means includes a normally substantially horizontal platform member 13 for supporting the brain tissue and a base 15 adjacent the platform member 13. The base 15 preferably includes a bottom portion 17, a back portion 19, a first side portion 21, and a second side portion 23. The platform member 13 is positioned above the bottom portion 17 of the base 15 adjacent the back portion 19, first side portion 21, and second side portion 23 thereof. The back portion 19 prevents the brain tissue supported on the platform member 13 from sliding backward a substantial amount as the autopsy knife is passed therethrough. Likewise, the first and second side portions 21, 23 prevent the brain tissue supported on the platform member 13 from sliding sideward a substantial amount as the autopsy knife is passed therethrough. The back portion 19 preferably includes a portion 25 which extends above the first and second side portions 21, 23 for a reason which will become apparent later in this description. The portion 25 is preferably composed of a substantially resilient material such as cork, which will protect the brain against damage when moved thereagainst and will aid in holding the brain against slippage. The bottom portion 17 of the base 13 may be provided with feet portions 27 for supporting the apparatus 11 above a supporting surface such as a table or the like. The guide means includes first and second guide portions 29, 31 adjacent the upper surface of the first and second side portions 21, 23. More specifically, the upper surfaces of the first and second side portions 21, 23 act as the first and second guide portions 29, 31 to guide the autopsy knife through the brain tissue as the brain tissue is supported on the platform member 13. It should be noted that the normal autopsy knife is of such a length as to extend across both the first and second guide portions 29, 31.

The apparatus 11 preferably includes an adjustment means 33 for raising and lowering the platform member 13 relative to the guide means to allow the brain tissue supported on the platform member 13 to be positioned at different locations relative to the first and second guide portions 29, 31 of the guide means thereby allowing the autopsy knife to be guided through a specific area of the brain tissue supported on the platform member 13. The adjustment means 33 may be any type of mechanism well known to those skilled in the art that will raise and lower the platform member 13. For example, the adjustment means 13 may be a lazy tong-type mechanism 35 having one end thereof attached to the bottom surface of the platform member 13 and having the other end thereof attached to the top surface of the bottom portion 17. The lazy tong-type mechanism 35 includes a screw-like member 37 having a knob 39 attached to one end thereof. It will be apparent to one skilled in the art that by turning the screw-like member 37 by means of the knob 39, the lazy tong-type mechanism 35 will cause the platform member 13 to be raised or lowered relative to the bottom portion 17 of the base 15 and, thus, to the first and second guide portions 29, 31.

The apparatus 11 preferably includes scale means located adjacent the guide means and the platform member 13 for allowing the platform member 13 to be adjusted a graduated degree relative to the guide means to allow the autopsy knife to be guided through a selected area of the brain tissue supported on the platform member 13. More specifically, the scale means preferably includes first and second scale members 41, 43 attached to the first and second side portions 21, 23 adjacent the platform member 13 and the first and second guide portions 29, 31 for allowing the distance between the top surface of the platform member 13 and the first and second guide portions 29, 31 to be indicated. Thus, when it is desired to cut into a desired portion of the brain tissue such as when an X-ray disclosed the possibility of a tumor or the like in a specific area of the brain tissue, the platform member 13 is simply raised or lowered relative to the first and second guide portions 29, 31 by the adjustment means 33 until that specific area of the brain tissue is adjacent the first and second guide portions 29, 31 as indicated by the first and second scale members 41, 43. In addition, the first and second scale members 41, 43 allow a section of desired thickness to be cut from the brain tissue. That is, to obtain a section of brain tissue of any desired thickness, a first cut is made by passing the autopsy knife through the brain tissue along the first and second guide portions 29, 31. Next, the platform member 13 is raised an amount equal to the desired thickness of brain tissue as indicated on the first and second scale members 41, 43. Finally, a second cut is made by passing the autopsy knife through the brain tissue along the first and second guide portions 29, 31 thereby giving a section of brain tissue of the desired thickness.

Figure 3:
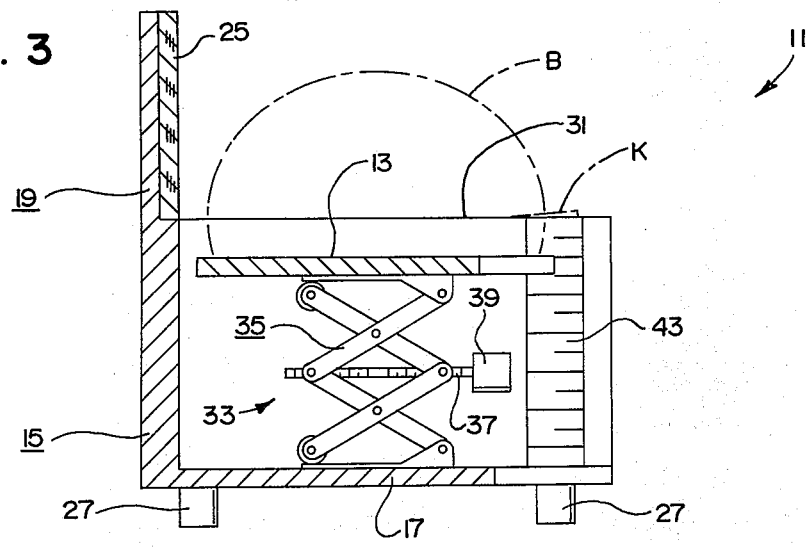
FIG. 3 is a sectional view of the autopsy apparatus of the present invention as taken on line III—III of FIG. 2, showing brain tissue and an autopsy knife in phantom lines.

The use of the apparatus 11 is quite simple. First, brain tissue B is placed upon the platform member 13 (see FIG. 3). The brain tissue B may be a complete brain or any portion thereof. Next, the platform member 13 is raised or lowered relative to the first and second guide portions 29, 31 until the desired section of the brain tissue B is adjacent the first and second guide portions 29, 31. Next, an autopsy knife K is guided through the brain tissue B along the first and second guide portions 29, 31 until it comes to the extended portion 25 of the back portion 19 of the base 15 which acts as a stop for the autopsy knife K. The platform member 13 can then be readjusted to allow any number of subsequent cuts through the brain tissue B as is desired.

As thus constructed and used, the present invention provides an apparatus which alleviates the problems associated with the cutting of brain tissue during an autopsy. That is, the present invention allows brain tissue to be easily cut during an autopsy by providing means for holding and restraining movement of the brain tissue as the autopsy knife is passed therethrough and means for guiding the autopsy knife through the brain tissue as the brain tissue is restrained. In addition, the present invention allows cuts to be accurately made into selected areas of the brain tissue.

Although the invention has been described and illustrated with respect to a preferred embodiment thereof, it is not to be so limited since changes and modifications may be made therein which are within the full intended scope of the invention.

I claim:

1. Apparatus for use in autopsies to assist in the cutting of brain tissue with an autopsy knife, said apparatus comprising:
   a. holding means for holding and restraining movement of the brain tissue as the autopsy knife is passed through the brain tissue;
   b. guide means located adjacent said holding means for guiding the autopsy knife through the brain tissue as the brain tissue is restrained by said holding means, said holding means including a horizontally disposed platform member for supporting the brain tissue, said horizontal platform member being movable relative to said guide means for allowing the brain tissue supported on said platform member to be positioned at different locations relative to said guide means, and
   c. scale means located adjacent said guide means and said movable platform member for allowing said movable platform member to be adjustably positioned in graduated degrees relative to said guide means thus the autopsy knife may selectively be guided through various predetermined areas of the brain tissue while being supported on said platform member.

2. The apparatus of claim 1 in which said holding means includes a back portion located adjacent said platform member for preventing the brain tissue supported on said platform member from sliding backward a substantial amount as the autopsy knife is passed through the brain tissue.

3. The apparatus of claim 2 in which said holding means includes first and second side portions located adjacent said platform member and said back portion for preventing the brain tissue supported on said platform member from sliding sideward a substantial amount as the autopsy knife is passed through the brain tissue.

4. The apparatus of claim 3 in which is included adjustment means for raising and lowering said platform means relative to said guide means.

5. Apparatus for use in autopsies to assist in the cutting of brain tissue with an autopsy knife, said apparatus comprising:
   a. holding means for holding and restraining movement of the brain tissue; said holding means including a platform member for supporting the brain tissue, a back portion located adjacent said platform member for preventing the brain tissue supported on said platform member from sliding backward a substantial amount as the autopsy knife is passed through the brain tissue, and first and second side portions located adjacent said platform member and said back portion for preventing the brain tissue supported on said platform member from sliding sideward a substantial amount as the autopsy knife is passed through the brain tissue;
   b. guide means located adjacent said platform member for guiding the autopsy knife through the brain tissue as the brain tissue is restrained by said holding means;
   c. adjustment means for raising and lowering said platform member relative to said guide means to allow the brain tissue supported on said platform member to be positioned at different locations relative to said guide means thereby allowing the autopsy knife to be guided through a specific area of the brain tissue supported on said platform member; and
   d. scale means located adjacent said guide means and said platform member for allowing said platform member to be adjusted a graduated degree relative to said guide means to allow the autopsy knife to be guided through a selected area of the brain tissue supported on said platform member.

6. The apparatus of claim 5 in which said adjustment means includes lazy tong-type mechanism having a screw-like member with a knob attached to one end thereof whereby selectively turning the knob actuates said lazy tong-type mechanism thus causing said platform member to be raised and lowered.

* * * * *